United States Patent [19]

Isogai et al.

[11] Patent Number: 4,552,986

[45] Date of Patent: Nov. 12, 1985

[54] PROCESS FOR PREPARATION OF ETHANOL

[75] Inventors: Nobuo Isogai; Takashi Okawa; Motoyuki Hosokawa; Nastuko Wakui; Toshiyasu Watanabe, all of Niigata, Japan

[73] Assignee: Mitsubishi Gas Chemical Company, Inc., Tokyo, Japan

[21] Appl. No.: 538,008

[22] Filed: Sep. 30, 1983

Related U.S. Application Data

[63] Continuation of Ser. No. 296,120, Aug. 25, 1981, abandoned.

[30] Foreign Application Priority Data

Sep. 5, 1980 [JP] Japan ................................ 55-123032

[51] Int. Cl.$^4$ ...................... C07C 29/00; C07C 31/08
[52] U.S. Cl. .................................................. 568/902
[58] Field of Search ........................................ 568/902

[56] References Cited

U.S. PATENT DOCUMENTS

| | | | |
|---|---|---|---|
| 2,623,906 | 12/1952 | Gresham | 568/902 |
| 3,248,432 | 4/1966 | Riley et al. | 568/902 |
| 3,285,948 | 11/1966 | Butter | 568/902 |
| 4,190,729 | 2/1980 | Forster | 568/902 |
| 4,205,190 | 5/1980 | Gane et al. | |
| 4,301,312 | 11/1981 | Feder et al. | |
| 4,304,946 | 12/1981 | Isogai et al. | 568/902 |
| 4,319,056 | 3/1982 | Gane et al. | |
| 4,328,375 | 5/1982 | Barlow | |
| 4,380,681 | 4/1983 | Barclay et al. | |

OTHER PUBLICATIONS

The Merck Index, Ninth edition, (1976), p. 313.

*Primary Examiner*—J. E. Evans
*Attorney, Agent, or Firm*—Armstrong, Nikaido, Marmelstein & Kubovcik

[57] ABSTRACT

Ethanol is prepared with high selectivity from methanol, carbon monoxide and hydrogen by using cobalt phosphate as main catalyst in combination with a platinum group element as co-catalyst or without using such co-catalyst, and further with or without a phosphorus compound. Recovery of the catalyst can be carried out easily.

37 Claims, No Drawings

PROCESS FOR PREPARATION OF ETHANOL

This is a continuation of application Ser. No. 296,120, filed August 25, 1981, now abandoned.

This invention relates to a process for preparing ethanol from methanol, carbon monoxide and hydrogen by using a novel catalyst.

For the preparation of ethanol from methanol, carbon monoxide and hydrogen, it is known to use a soluble cobalt salt or a ruthenium compound or osmium compound as a main catalyst in combination with iodine, bromine or a compound thereof and further with or without a phosphorus compound, and such known composite catalysts are all used as a homogeneous system.

However, in use of such conventional catalyst systems for the ethanol preparation reactions, although they show, in some cases, a relatively high selectivity for the objective material ethanol, they involve various problems such as mentioned below for industrial use.

Since the combined use of such elements as iodine or bromine is indispensable for said conventional catalyst systems, it needs to use a highly corrosion-resistant expensive material for the apparatus and also a complicated process is required for the catalyst recovery. Further, as the catalytic active components are unstable, much loss is suffered in catalyst recovery and it is hardly possible to recover the catalyst with the active components maintained. Therefore, for reuse of the recovered catalyst, it is required to reprepare the catalyst by freshly supplying the lost portion. Thus, the ethanol preparation process using the conventional catalyst systems necessitates a high catalyst cost and can hardly be deemed as a practical method for commercial production of ethanol.

A process for preparing ethanol based on use of at least cobalt sulfide as a cobalt catalyst was proposed by the present applicant (U.S. patent application Ser. No. 144,990). However, it has been found that the process has such a disadvantage that recovery of the catalyst is difficult to carry out, since some of catalyst turns colloid, and the product ethanol sometimes has a disagreeable odor, which seems due to thiocarbonyl.

As a result of further studies for eliminating said various problems in the prior art, the present inventors found that if cobalt phosphate is used as main catalyst, it is possible to synthesize ethanol with high selectivity, with no need of combined use of iodine, bromine, etc., and the present invention was completed on the basis of such finding.

Thus, the present invention provides a process for preparing ethanol from methanol, carbon monoxide and hydrogen, characterized by using cobalt phosphate as main catalyst in combination with a platinum group element as co-catalyst or without using such co-catalyst, and further with or without a phosphorus compound, said catalyst being used as a heterogeneous system.

The cobalt phosphate used in this invention may be either an anhydride or hydrate, and such cobalt phosphate is used in an insoluble state. More specifically, it may be used in a powdery state dispersed in the reaction system or may be used as a packed layer by molding said material to a suitable size. It may be also used in a state supported by a carrier such as active carbon, silica, alumina, diatomaceous earth and zeolite.

In the present invention, a platinum group element (5th and 6th Periods of Group VIII in the Periodic Table) may be used as co-catalyst. Such platinum group elements are ruthenium, rhodium, palladium, osmium, iridium and platinum, but ruthenium, rhodium and palladium (5th Period of Group VIII) are preferred. Use of such co-catalyst can control by-production of the oxygenated compounds other than ethanol. Any suitable form may be taken in use of said elements as co-catalyst provided that the co-catalyst is insoluble in the reaction system. For instance, said elements may be used in the form of oxide, chloride or fluoride or as catalyst components supported by a carrier such as active carbon. Especially, oxide, chloride and carrier-supported metal are preferred.

The present invention can be performed according to either a continuous or batch-type method using a fixed, fluidized or moving bed.

The amount of the catalyst used is not critical in the case of the continuous method using a fixed bed, but in other cases, it is defined as follows.

The amount of cobalt phosphate used as catalyst, although variable depending on the mode of use, is practically 0.1–500 milliatoms as calculated in terms of metallic cobalt per mole of methanol. If the amount of cobalt phosphate is less than the above range, although the reaction can advance, the reaction rate is low. Use of cobalt phosphate in a greater amount causes no adverse effect to the reaction, but practically the above-defined range suffices for the intended reaction. The preferred range is 1–200 milliatoms.

The amount of the co-catalyst used is not subject to any specific limitations, but practically it is used in an amount of 0.01–50 milliatoms, preferably 0.1–20 milliatoms, as calculated in terms of metal per mole of methanol. The effect of use of co-catalyst is well manisfested in said amount range.

The ratio of main catalyst to co-catalyst is not limited to any specified range but any suitable ratio may be selected to satisfy the above-defined ranges of the respective catalysts. This ratio can apply to the catalysts used as packed layer in fixed-bed continuous method.

Further, in the present invention, the catalytic activity can be elevated by incorporating a phosphorus compound in the catalyst system. As such phosphorus compound, alkylphosphine or phosphine oxide is most effective. The amount of such phosphorus compound used, though not defined specifically, is practically 0.1–200 millimoles, preferably 1–50 millimoles per mole of methanol.

In the present invention, a reaction medium may or may not be used. Any suitable material may be used as the reaction medium in this invention provided that such material does not dissolve the catalyst, but usually an organic solvent is used. Exemplary of the preferable reaction media for use in this invention are hydrocarbons such as hexane, octane, cyclohexane, benzene and toluene; oxygenated compounds such as methyl acetate, dioxane and tetrahydrofuran; formamides, acetoamides, pyrrolidones, acetonitriles and amines such as pyridine and lutidine. Among them, methyl acetate is most preferred. A mixture of the organic solvents may be used as reaction media. The amount of the reaction medium used is not subject to any specific limitations, but practically it is used in an amount of 0.01–5 moles, preferably 0.05–1 mole per mole of methanol.

The reaction conditions in this invention may be those commonly used for this type of reaction. Carbon monoxide and hydrogen may be used in a stoichiometrical amount or greater as against methanol. The carbon dioxide:hydrogen molar ratio is within the range of 4:1 to 1:4, preferably 2:1 to 1:2. Any reaction pressure not higher than 600 kg/cm$^2$ may be used in this invention, but preferably it is 50 kg/cm$^2$ or higher, and practically the range of 150-450 kg/cm$^2$ is most preferred.

Both carbon monoxide and hydrogen used for the reaction of this invention may be mixed with an inert gas such as argon, nitrogen, carbon dioxide, methane or ethane, but in this case, the partial pressures of carbon monoxide and hydrogen must be adjusted so that the sum thereof will correspond to the above-defined pressure range.

The reaction temperature may vary depending on the catalyst system used and other reaction conditions, but usually it is within the range of 150°-350° C., preferably 180°-280° C. The reaction can advance at a temperature below 150° C., but the reaction rate is low. Use of a temperature above 350° C. tends to cause unfavorable side-reactions.

The process of this invention is capable of minimizing formation of by-products and obtaining free ethanol with high selectivity, and the used catalyst can be separated and recovered by a simple filtration operation. The catalyst recovered may be reused. Also, the recovery loss is small. Thus, the ethanol preparation process of this invention is quite useful and advantageous for industrial applications.

The process of this invention is described in further detail hereinbelow by way of the embodiments thereof.

EXAMPLE 1

15 g of methanol and 3 g of powder of cobalt phosphate[Co$_3$(PO$_4$)$_2$.8H$_2$O] as catalyst (Co$_3$(PO$_4$)$_2$.8H$_2$O was used as cobalt phosphate in the succeeding Examples, too) were added into a stainless-steel shaking type autoclave having an inner capacity of 100 ml, followed by feed under pressure of a mixture gas of hydrogen and carbon monoxide (H$_2$/CO molar ratio=1) at a pressure of 200 kg/cm$^2$ to perform a reaction at 250° C. for 3 hours.

The methanol conversion was 8.6 mol% and the selectivity to ethanol was 89.2%.

EXAMPLE 2

15 g of methanol and 5 g of methyl acetate as reaction medium were supplied into said type of autoclave by using the same catalyst in the same amount as used in Example 1, and they were reacted under the same conditions as in Example 1.

The methanol conversion was 12.0 mol% and the selectivity to ethanol was 90.3%.

EXAMPLE 3

10 g of methanol, 3 g of cobalt phosphate and 1 g of active carbon-supported ruthenium (Ru—C) with 5% ruthenium content, and 1 g of tributylphosphine as catalyst, and 2 g of methyl acetate were added into said type of autoclave and reacted under the same conditions as in Example 1.

The methanol conversion was 16.2 mol% and the selectivity to ethanol was 92.0%.

EXAMPLE 4

10 g of methanol, 2 g of cobalt phosphate and 2 g of tributylphosphine as catalyst, 4 g of N-methyl-2-pyrrolidone and 2 g of methyl acetate were added and reacted under the same conditions as in Example 1.

The methanol conversion was 14.4 mol% and the selectivity to ethanol was 88.0%.

EXAMPLE 5

3 g of cobalt phosphate and 1 g of active carbon-supported palladium (Pd—C) with 5% palladium content as catalyst were added to 10 g of methanol, followed by further addition of 5 g of n-octane and 2 g of methyl acetate as reaction medium and they were reacted under the same conditions as in Example 1.

The methanol conversion was 15.0 mol% and the selectivity to ethanol was 91.1%.

EXAMPLE 6

3 g of cobalt phosphate and 1 g of active carbon-supported rhodium (Rh—C) with 5% rhodium content as catalyst were added to 10 g of methanol, followed by further addition of 5 g of tetrahydrofuran as reaction medium, and a mixture gas of hydrogen and carbon monoxide (H$_2$/CO molar ratio=1) was fed thereto at a pressure of 200 kg/cm$^2$, and they were reacted at 220° C. for 3 hours.

The methanol conversion was 12.5 mol% and the selectivity to ethanol was 84.0%.

What is claimed is:

1. A process for preparing ethanol from methanol, carbon monoxide and hydrogen, which comprises using an insoluble catalyst selected from the group consisting of the following two catalyst:
   the first catalyst consisting of one of a powdery cobalt phosphate, a molded cobalt phosphate, and cobalt phosphate supported on a carrier; and
   the second catalyst consisting of (a) one of a powdery cobalt phosphate, a molded cobalt phosphate, and cobalt phosphate supported on a carrier plus (b) at least one of a platinum group metal itself, an oxide of a platinum group metal, a chloride of a platinum group metal, a fluoride of a platinum group metal supported on a carrier, and an alkyl phosphine.

2. A process for preparing ethanol from methanol, carbon monoxide and hydrogen, which comprises using an insoluble catalyst consisting of (a) one of powdery cobalt phosphate, a molded cobalt phosphate and cobalt phosphate supported on the carrier, and (b) at least one of a platinum group metal itself, an oxide of a platinum group metal, a chloride of a platinum group metal, a fluoride of a platinum group metal, a platinum group metal supported on a carrier, and an alkyl phosphine.

3. A process according to claim 2, wherein the platinum group metal is selected from the group consisting of Ru, Rh, Pd, Os, Ir, and Pt.

4. A process according to claim 2, wherein the platinum group metal is a metal selected from the group consisting of Group VIII and period V of the Periodic Table.

5. A process according to claim 2, wherein reaction is carried out continuously or batchwise in a fixed bed, fluidized bed or moving bed.

6. A process according to claim 2, wherein the cobalt phosphate is used in an amount of 0.1-500 milliatoms in terms of metallic cobalt per mole of methanol.

7. A process according to claim 2, wherein the platinum group metal is used in an amount of 0.01-50 milliatoms in terms of metal per mole of methanol.

8. A process according to claim 2, wherein 0.1–200 millimoles of the phosphorus compound is used per mole of methanol.

9. A process according to claim 2, wherein a reaction medium is used.

10. A process according to claim 2, wherein 0.01–5 moles of a reaction medium per mole of methanol is used.

11. A process according to claim 2, wherein a molar ratio of the carbon monoxide to the hydrogen is 4:1–1:4.

12. A process according to claim 2, wherein reaction is carried out at a pressure of 600 kg/cm$^2$ or less.

13. A process according to claim 2, wherein reaction is carried out at a temperature of 150°–350° C.

14. A process according to claim 2, wherein the catalyst consists of (a) one of the powdery cobalt phosphate, the molded cobalt phosphate and the cobalt phosphate supported on the carrier and (b) one of the platinum group metal itself, the oxide of a platinum group metal, the chloride of a platinum group metal, the fluoride of a platinum group metal and the platinum group metal supported on a carrier.

15. A process according to claim 2, wherein the catalyst consists of (a) one of the powdery cobalt phosphate, the molded cobalt phosphate and the cobalt phosphate supported on the carrier and (b) the alkyl phosphine.

16. A process according to claim 2, wherein the catalyst consists of (a) one of the powdery cobalt phosphate, the molded cobalt phosphate and the cobalt phosphate supported on a carrier, (b) one of the platinum group metal itself, the oxide of a platinum group metal, the chloride of a platinum group metal, the fluoride of a platinum group metal and the platinum group metal supported on a carrier, and (c) the alkyl phosphine.

17. A process according to claim 2, wherein the catalyst is selected from the group consisting of the following two catalysts, the first catalyst consisting of the cobalt phosphate supported on a carrier, and the second catalyst consisting of (a) the powdery cobalt phosphate supported on a carrier and (b) at least one of the platinum group metal supported on a carrier and alkyl phosphine.

18. A process for preparing ethanol from methanol, carbon monoxide and hydrogen, which comprises using an insoluble catalyst not containing iodine and comprising cobalt phosphate and at least one compound of a platinum group metal and an alkyl phosphine.

19. A process according to claim 18, wherein the catalyst is supported on a carrier.

20. A process according to claim 1, wherein the platinum group metal is selected from the group consisting of Ru, Rh, Pd, Os, Ir, and Pt.

21. A process according to claim 1, wherein the platinum group metal is a metal selected from the group consisting of Group VIII and period V of the Periodic Table.

22. A process according to claim 1, wherein reaction is carried out continuously or batchwise in a fixed bed, fluidized bed or moving bed.

23. A process according to claim 1, wherein the cobalt phosphate is used in an amount of 0.1–500 milliatoms in terms of metallic cobalt per mole of methanol.

24. A process according to claim 1, wherein the platinum group metal is used in an amount of 0.01–50 milliatoms in terms of metal per mole of methanol.

25. A process according to claim 1, wherein 0.1–200 millimoles of the alkyl phosphine is used per mole of methanol.

26. A process according to claim 1, wherein a reaction medium is used.

27. A process according to claim 1, wherein 0.01–5 moles of a reaction medium per mole of methanol is used.

28. A process according to claim 1, wherein a molar ratio of the carbon monoxide to the hydrogen is 4:1–1:4.

29. A process according to claim 1, wherein reaction is carried out at a pressure of 600 kg/cm$^2$ or less.

30. A process according to claim 1, wherein reaction is carried out at a temperature of 150°–350° C.

31. A process according to claim 1, wherein the catalyst consists of (a) one of the powdery cobalt phosphate, the molded cobalt phosphate and the cobalt phosphate supported on the carrier and (b) one of the platinum group metal itself, the oxide of a platinum group metal, the chloride of a platinum group metal, the fluoride of a platinum group metal and the platinum group metal supported on a carrier.

32. A process according to claim 1, wherein the catalyst consists of (a) one of the powdery cobalt phosphate, the molded cobalt phosphate and the cobalt phosphate supported on the carrier and (b) the alkyl phosphine.

33. A process according to claim 1, wherein the catalyst consists of (a) one of the powdery cobalt phosphate, the molded cobalt phosphate and the cobalt phosphate supported on a carrier, (b) one of the platinum group metal itself, the oxide of a platinum group metal, the chloride of a platinum group metal, the fluoride of a platinum group metal and the platinum group metal supported on a carrier, and (c) the alkyl phosphine.

34. A process according to claim 1, wherein the catalyst is selected from the group consisting of the following two catalysts, the first catalyst consisting of the cobalt phosphate supported on a carrier, and the second catalyst consisting of (a) the powdery cobalt phosphate supported on a carrier and (b) at least one of the platinum group metal supported on a carrier and the alkyl phosphine.

35. A process for preparing ethanol from methanol, carbon monoxide and hydrogen, which comprising using an insoluble catalyst consisting of cobalt phosphate and at least one compound of a platinum group metal and an alkyl phosphine.

36. A process according to claim 1, wherein the methanol is in a liquid phase.

37. A process according to claim 2, wherein the methanol is used in a liquid phase.

* * * * *